(12) United States Patent
Okita

(10) Patent No.: US 7,688,436 B2
(45) Date of Patent: Mar. 30, 2010

(54) MEASURING AND/OR INSPECTING METHOD, MEASURING AND/OR INSPECTING APPARATUS, EXPOSURE METHOD, DEVICE MANUFACTURING METHOD, AND DEVICE MANUFACTURING APPARATUS

(75) Inventor: Shinichi Okita, Nishitokyo (JP)

(73) Assignee: Nikon Corporation, Tokyo (JP)

( * ) Notice: Subject to any disclaimer, the term of this patent is extended or adjusted under 35 U.S.C. 154(b) by 130 days.

(21) Appl. No.: 11/785,865

(22) Filed: Apr. 20, 2007

(65) Prior Publication Data

US 2007/0259290 A1 Nov. 8, 2007

Related U.S. Application Data

(60) Provisional application No. 60/905,817, filed on Mar. 9, 2007.

(30) Foreign Application Priority Data

Apr. 27, 2006 (JP) ............................. 2006-123123

(51) Int. Cl.
*G01N 21/00* (2006.01)
(52) U.S. Cl. ............................. 356/237.4; 356/237.1
(58) Field of Classification Search ... 356/237.1–241.6, 356/426–431, 600–640
See application file for complete search history.

(56) References Cited

U.S. PATENT DOCUMENTS

| | | | |
|---|---|---|---|
| 3,615,463 A * | 10/1971 | Kuschell | 430/312 |
| 4,334,156 A * | 6/1982 | Bohlen et al. | 250/491.1 |
| 4,748,327 A * | 5/1988 | Shinozaki et al. | 250/358.1 |
| 4,778,275 A * | 10/1988 | van den Brink et al. | 356/401 |
| 5,370,975 A | 12/1994 | Nakatani | |
| 5,479,537 A * | 12/1995 | Hamashima et al. | 382/266 |
| 5,821,131 A * | 10/1998 | Bae | 438/16 |
| 5,825,043 A | 10/1998 | Suwa | |
| 5,825,647 A * | 10/1998 | Tsudaka | 430/5 |
| 5,838,433 A * | 11/1998 | Hagiwara | 356/364 |
| 6,038,015 A * | 3/2000 | Kawata | 355/67 |
| 6,327,022 B1 * | 12/2001 | Nishi | 355/53 |
| 6,404,481 B1 * | 6/2002 | Feldman et al. | 355/52 |
| 6,634,290 B1 * | 10/2003 | Shimizu et al. | 101/129 |
| 6,701,004 B1 * | 3/2004 | Shykind et al. | 382/149 |
| 6,757,645 B2 * | 6/2004 | Chang et al. | 703/13 |
| 2001/0004765 A1 | 6/2001 | Miyagawa | |

(Continued)

FOREIGN PATENT DOCUMENTS

JP    A-05-273739    10/1993

(Continued)

*Primary Examiner*—Gregory J Toatley, Jr.
*Assistant Examiner*—Jarreas C Underwood
(74) *Attorney, Agent, or Firm*—Oliff & Berridge, PLC

(57) ABSTRACT

In the inspection of one reticle of reticles used for double exposure, the pattern area of the reticle is divided into a plurality of areas, according to (a) whether an area is a light-transmitting section or a light-shielding section, (b) whether a pattern area of the other reticle is a light-transmitting section, a light-shielding section, or a proximity section to a pattern, and the like, and inspection conditions are changed with respect to each area so that abnormality that is directly related to the yield can be detected. Thus, the defect inspection of the reticles that is directly related to the yield of device production can be performed.

19 Claims, 7 Drawing Sheets

U.S. PATENT DOCUMENTS

| | | | |
|---|---|---|---|
| 2002/0103607 A1* | 8/2002 | Crell | 702/34 |
| 2003/0056184 A1* | 3/2003 | Noda | 716/5 |
| 2004/0018436 A1* | 1/2004 | Ishikawa | 430/5 |

FOREIGN PATENT DOCUMENTS

| | | |
|---|---|---|
| JP | 6-124873 | 5/1994 |
| JP | A 10-209039 | 8/1998 |
| JP | A 10-303114 | 11/1998 |
| JP | A 11-135400 | 5/1999 |
| JP | A 2000-164504 | 6/2000 |
| JP | A-2001-174977 | 6/2001 |
| JP | A-2001-250756 | 9/2001 |
| JP | A-2004-191297 | 7/2004 |
| WO | WO 98/24115 A1 | 6/1998 |
| WO | WO 98/40791 A1 | 9/1998 |
| WO | WO 99/49504 A1 | 9/1999 |

* cited by examiner

*Fig. 7*

| PA1 | | PA2 | | AREA NAME | SENSITIVITY | PERMISSIBLE SIZE |
|---|---|---|---|---|---|---|
| 1ST ATTRIBUTE | 1ST ATTRIBUTE | 2ND ATTRIBUTE | 3RD ATTRIBUTE | | | |
| LIGHT-TRANSMITTING SECTION | LIGHT-TRANSMITTING SECTION | AREAS OTHER THAN PROXIMITY AREA | | AREA A | STANDARD | LARGE |
| | | PROXIMITY AREA | CONVENTIONAL PATTERN | AREA B | HIGH | STANDARD |
| | | | CONTACT HOLE PATTERN | AREA C | HIGH | STANDARD |
| | | | PHASE SHIFT PATTERN | AREA D | HIGH | STANDARD |
| | | | OPC PATTERN | AREA E | HIGH | STANDARD |
| | LIGHT-SHIELDING SECTION | | | AREA F | STANDARD | SMALL |
| LIGHT-SHIELDING SECTION | | | | AREA G | STANDARD | LARGE |

MEASURING AND/OR INSPECTING METHOD, MEASURING AND/OR INSPECTING APPARATUS, EXPOSURE METHOD, DEVICE MANUFACTURING METHOD, AND DEVICE MANUFACTURING APPARATUS

CROSS-REFERENCE TO RELATED APPLICATIONS

This non-provisional application claims the benefit of Provisional Application No. 60/905,817 filed Mar. 9, 2007, the disclosure of which is hereby incorporated herein by reference in its entirety.

BACKGROUND OF THE INVENTION

1. Field of the Invention

The present invention relates to measuring and/or inspecting methods, measuring and/or inspecting apparatuses, exposure methods, device manufacturing methods and device manufacturing apparatuses, and more particularly, to a measuring and/or inspecting method in which at least one of a plurality of masks that are placed on an optical path of each of a plurality of exposure lights irradiated to the same area of an area to be exposed on a substrate is measured and/or inspected, an measuring and/or inspecting apparatus that uses the measuring and/or inspecting method, an exposure method in which a plurality of exposure lights are irradiated to an area to be exposed on a substrate, a device manufacturing method that includes an exposure process in which a plurality of exposure lights are irradiated to an area to be exposed on a substrate, and a device manufacturing apparatus that uses the device manufacturing method.

2. Description of the Background Art

Conventionally, from the viewpoint of throughput, the defect inspection of a pattern formation surface of a reticle (mask) is implemented not immediately before exposure, but after reticle manufacturing or at the time of periodic inspection, or the like. However, recently, for the purpose of improving resolution of a device pattern to be transferred on a substrate and the like, a so-called multiple exposure method has been used in which a plurality of patterns are transferred and overlaid to the same area on the surface to be exposed of the substrate (e.g. refer to Kokai (Japanese Unexamined Patent Application Publications) No. 10-209039). In the multiple exposure method, since an effective area size of a pattern to which an exposure light is irradiated is larger, compared with the case of a conventional exposure method, the necessity of defect inspection of the pattern formation surface on a reticle immediately before exposure is increasing.

In the reticle defect inspection immediately before exposure, only the defect that affects the yield of device production is preferably inspected, from the viewpoint of improving the throughput. In the multiple exposure method, however, the exposure result on the substrate is the overlay transfer result of patterns on a plurality of reticles, and therefore, it is extremely difficult to distinguish the defect that is directly related to the yield of device production from other defects on the pattern formation surface, compared with the case of the conventional exposure method.

SUMMARY OF THE INVENTION

The present invention has been made under such circumstances, and according to a first aspect of the present invention, there is provided a measuring and/or inspecting method in which at least one of a plurality of masks that are placed on an optical path of each of a plurality of exposure lights irradiated to a same area of an area to be exposed on a substrate is measured and/or inspected, the method comprising: changing, in accordance with information on a first pattern that is formed on a first mask of the plurality of masks, a processing content of a measurement and/or inspection processing related to a second mask of the plurality of masks that is different from the first mask.

With this method, a processing content of the measurement and/or inspection processing of each of a plurality of masks that are used for exposure to the same area on a substrate is changed in accordance with information on other masks. Thus, the measurement and/or inspection of masks that is directly related to the yield of device production can be performed in which not only an exposure state by an individual mask but also a comprehensive exposure state in the same area of an area to be exposed on the substrate are taken into consideration.

According to a second aspect of the present invention, there is provided a measuring and/or inspecting method in which at least one of a plurality of masks that are placed on an optical path of each of a plurality of exposure lights irradiated to a same area of an area to be exposed on a substrate is measured and/or inspected, the method comprising: a process in which total dose of the plurality of exposure lights irradiated to a same area of the area to be exposed is obtained.

With this method, the measurement and/or inspection of masks that is directly related to the yield of device production can be performed in which not only an exposure dose by each exposure light via an individual mask but also the total dose (total of light quantity) of a plurality of exposure lights irradiated to the same area of an area to be exposed on the substrate are taken into consideration.

According to a third aspect of the present invention, there is provided an exposure method in which a plurality of exposure lights are irradiated to an area to be exposed on a substrate, the method comprising: performing, in accordance with information on a first pattern formed on a first mask of a plurality of masks that are placed on an optical path of each of the plurality of exposure lights, a measurement and/or inspection processing of a second mask that is different from the first mask; and controlling an exposure processing of the substrate based on a result of the measurement and/or inspection processing.

With this method, based on a measurement and/or inspection result of the second mask using information on the first pattern formed on the first mask among a plurality of masks that are placed on each optical path of a plurality of exposure lights, that is, based on a comprehensive measurement and/or inspection result that relates to the plurality of masks, an exposure processing of the substrate can be controlled. Thus, exposure with high accuracy using the masks that pass the comprehensive measurement and/or inspection can be performed.

According to a fourth aspect of the present invention, there is provided a device manufacturing method that includes an exposure process in which a plurality of exposure lights are irradiated to an area to be exposed on a substrate, the method comprising: a process in which in accordance with information on a first pattern formed on a first mask of a plurality of masks that are placed on an optical path of each of the plurality of exposure lights, a second mask that is different from the first mask is measured and/or inspected.

With this method, measurement and/or inspection of masks that is directly related to the yield can be performed in which not only an exposure state by an individual mask but also a comprehensive exposure state in the same area of an area to be exposed on the substrate are taken into consideration, and therefore the yield of device production is improved.

According to a fifth aspect of the present invention, there is provided a device manufacturing method that includes an exposure process in which a plurality of exposure lights are irradiated to an area to be exposed on a substrate, the method comprising: executing, based on total dose of the plurality of exposure lights irradiated to a predetermined position of the area to be exposed via each of a plurality of masks that are placed on an optical path of each of the plurality of exposure lights, a predetermined processing to the masks.

With this method, since a predetermined processing is executed to the masks based on the total dose of a plurality of exposure lights, the yield of devices that are produced by multiple exposure can be improved.

According to a sixth aspect of the present invention, there is provided an exposure method in which an object is exposed by simultaneously or sequentially forming images of a plurality of patterns on a same area on the object, the method comprising: executing a measurement and/or inspection processing of an area, in which one of the plurality of patterns that are formed on a same mask or a different mask is formed, taking information on at least one of the remaining patterns of the plurality of patterns into consideration; and controlling an exposure condition of the object based on a result of the measurement and/or inspection processing.

With this method, based on a result of measurement and/or inspection of an area having a pattern formed thereon in which information on another pattern among the plurality of patterns that are formed on the same mask or different masks is taken into consideration, that is, based on a comprehensive measurement and/or inspection result that relates to the plurality of patterns, exposure conditions of the object can be controlled. Thus, exposure with high accuracy using the plurality of patterns that pass the comprehensive measurement and/or inspection can be performed.

BRIEF DESCRIPTION OF THE DRAWINGS

In the accompanying drawings:

FIG. 7 is a table in which the criteria used when creating an inspection condition map are described.

DESCRIPTION OF THE EMBODIMENTS

An embodiment of the present invention will be described below, referring to FIGS. 1 to 7.

Figure 1:
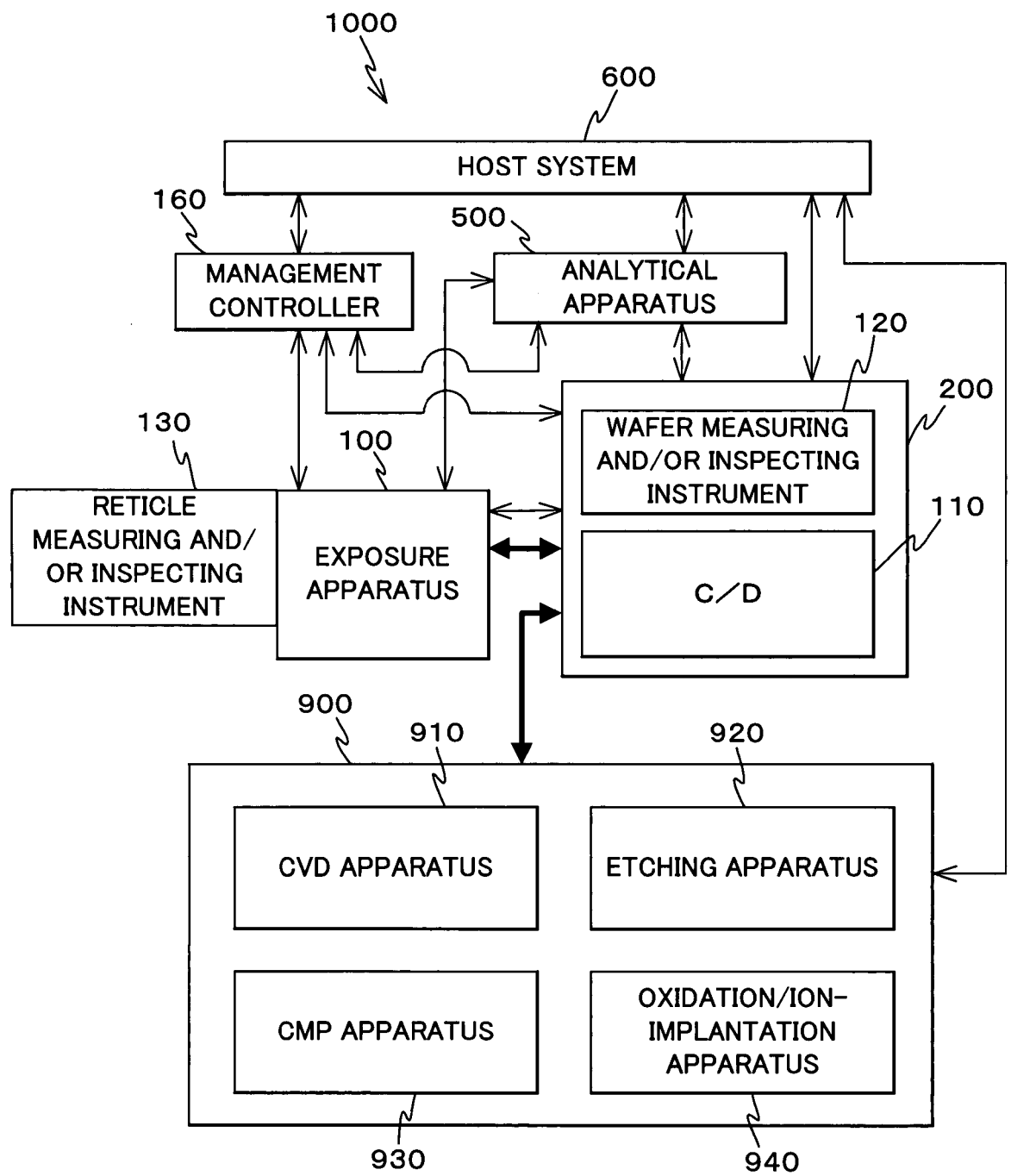
FIG. 1 is a schematic view showing a configuration of a device manufacturing system related to an embodiment.

FIG. 1 shows the schematic configuration of a device manufacturing system 1000 related to an embodiment. Device manufacturing system 1000 is a system that is constructed in a device manufacturing plant for manufacturing microdevices by processing semiconductor wafers. As is shown in FIG. 1, device manufacturing system 1000 is equipped with an exposure apparatus 100, a track 200 that is placed adjacent to exposure apparatus 100, a management controller 160, an analytical apparatus 500, a host system 600 and a device manufacturing apparatus group 900.

Figure 2:
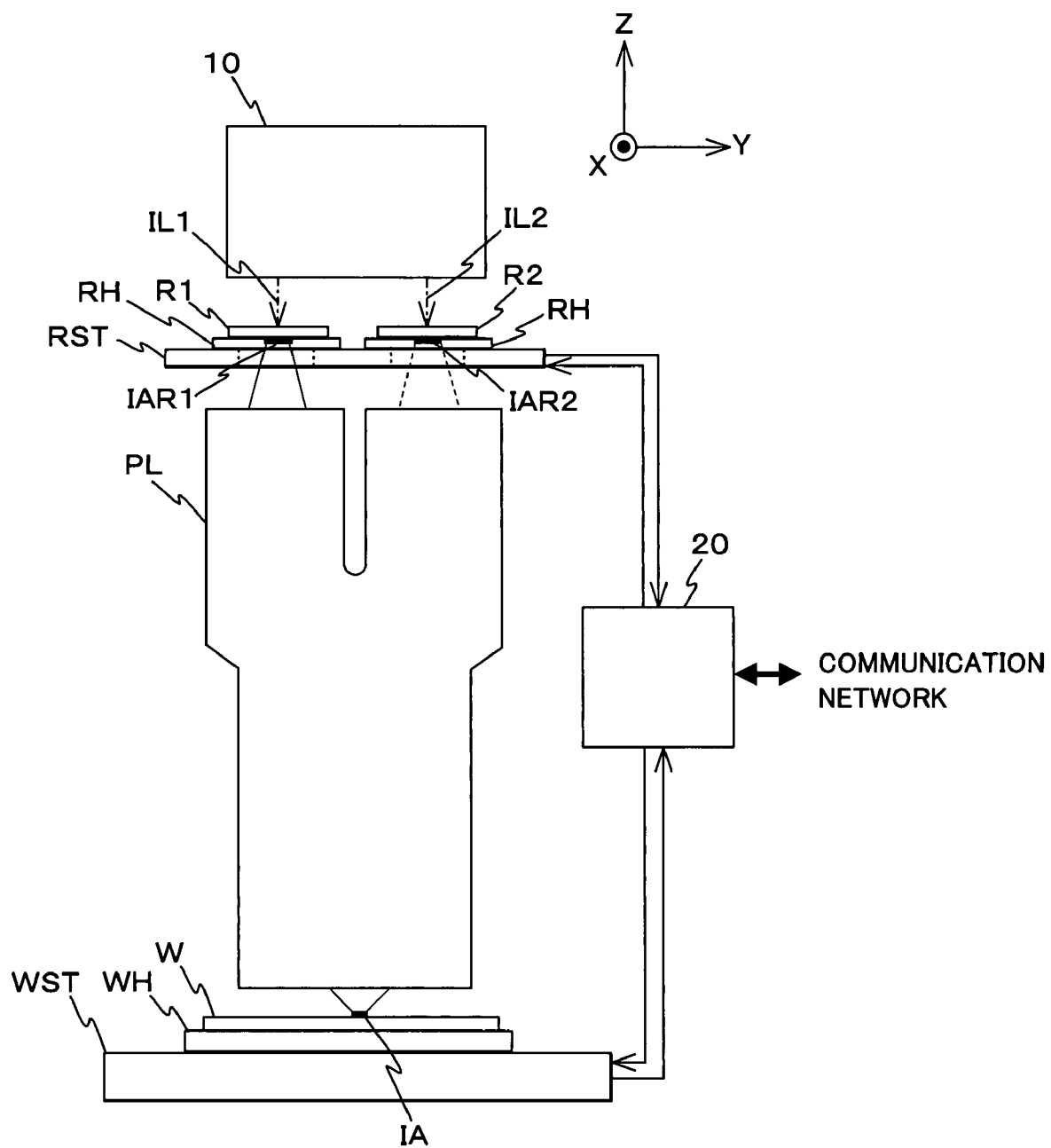
FIG. 2 is a schematic view showing a configuration of an exposure apparatus related to the embodiment.

Exposure apparatuses 100 is an apparatus that transfers a device pattern onto a wafer that is coated with photoresist. FIG. 2 shows the schematic configuration of exposure apparatus 100. Exposure apparatus 100 is equipped with an illumination system 10 that emits exposure lights IL1 and IL2, a reticle stage RST that holds a reticle R1, on which a device pattern and the like that are illuminated by exposure light IL1 are formed, and a reticle R2, on which a device pattern and the like that are illuminated by exposure light IL2 are formed, respectively via reticle holder RH, a both-side telecentric projection optical system PL that projects part of the device patterns formed on reticles R1 and R2 respectively that have been illuminated by exposure lights IL1 and IL2 on the surface to be exposed of a wafer W, a wafer stage WST that holds wafer W that becomes subject to exposure via a wafer holder WH, a main controller 20 that performs overall control of these constituents, and the like.

On each of reticles R1 and R2, a device pattern including a circuit pattern and the like is formed. Exposure lights IL1 and IL2 from illumination system 10 are irradiated on part of the pattern formation surfaces of reticles R1 and R2 respectively. Irradiation areas of exposure lights IL1 and IL2 are to be illumination areas IAR1 and IAR2, respectively.

Exposure lights IL1 and IL2 respectively via illumination areas IAR1 and IAR2 are incident on part of the surface to be exposed of wafer W (wafer surface) held on wafer stage WST via projection optical system PL, and projected images of the device patterns of illumination areas IAR1 and IAR2 are formed on the surface to be exposed in an overlay manner. An area in which the projected images are formed is to be an exposure area IA. The surface to be exposed of wafer W is coated with photoresist, and patterns of the projected images are transferred to a portion corresponding to exposure area IA.

Herein, an XYZ coordinate system that uses a coordinate axis along an optical axis of projection optical system PL as a Z-axis will be considered. Wafer stage WST can move within an XY plane, and also can adjust the surface to be exposed of wafer W in a Z-axis direction, a θx (rotation around an X-axis) direction and a θy (rotation around a Y-axis) direction. Further, reticle stage RST holding reticles R1 and R2 can move within the XY plane synchronously with wafer stage WST holding wafer W.

By the synchronous scanning of reticle stage RST and wafer stage WST in accordance with a projection magnification of projection optical system PL, the surface to be exposed of wafer W passes through exposure area IA synchronously with the device patterns on reticles R1 and R2 passing through illumination areas IAR1 and IAR2. With this operation, the device patterns of the entire pattern formation surfaces on reticles R1 and R2 are transferred to a partial area (shot area) on the surface to be exposed of wafer W. Exposure apparatus 100 transfers the device patterns on reticles R1 and R2 to a plurality of shot areas on wafer W by repeating the relative synchronous scanning of reticle stage RST and wafer stage WST with respect to exposure lights IL1 and IL2 described above and the stepping of wafer stage WST holding wafer W. That is, exposure apparatus 100 is an exposure apparatus by a scanning exposure (step-and-scan) method that performs so-called multiple exposure (double exposure).

In exposure apparatus 100, reticle holder RH is not integrally formed with reticle stage RST, and therefore is detachable. As a matter of course, reticle holder RH can be detached/attached also in a state of not holding reticles R1 and R2, and can be exchanged by a reticle holder exchanger (not shown).

Main controller 20 is a computer system that controls respective constituents of exposure apparatus 100. Main controller 20 is connected to a communication network that is set up within device manufacturing system 1000, and data can be sent to and received from the outside via the communication network.

Referring back to FIG. 1, a reticle measuring and/or inspecting instrument 130 that inspects reticles R1 and R2 to be used for exposure before the reticles are loaded on reticle stage RST is inline connected to exposure apparatus 100. Reticle measuring and/or inspecting instrument 130 performs various kinds of measurement and/or inspection of reticles R1 and R2.

The pattern formation surface of reticles R1 and R2 is a glass surface, and basically, a pattern area is formed on the pattern formation surface by depositing metals such as chromium to the glass surface to form a metal film and performing patterning to the metal film. Hereinafter, a pattern formed in the pattern area is also referred to as a chromium pattern.

Reticle measuring and/or inspecting instrument 130 detects defects of the pattern formation surface by performing an appearance inspection of the pattern formation surface of reticles R1 and R2. The defects are classified into hard defects and soft defects. The hard defects include a crack of a chromium pattern, residual of an unnecessary chromium pattern, a glass flaw and the like. And, the soft defects include dusts, stains, foreign particles and the like. The hard defects cannot be removed by chemical and mechanical cleaning processes, while the soft defects can be removed by these cleaning processes. In the appearance inspection, the hard defects and the soft defects of the pattern formation surface are detected.

The pattern formation surface of reticles R1 and R2 can be divided into a light-transmitting section and a light-shielding section. With regard to the defects on the light-transmitting section, the pattern formation surface is illuminated and the pattern formation surface is imaged from the back side, and the defects are detected based on the imaging results. Reticle measuring and/or inspecting instrument 130 performs chip comparison (die-to-die comparison) or data comparison (die-to-DB (database) comparison) to the pattern that has been imaged by a transmitted light, thereby detecting the differences obtained in the comparison result as the defects in the light-transmitting section. Generally, the defect detection sensitivity of reticle measuring and/or inspecting instrument 130 is set to around one third of the design pattern rule on standard. For example, in the case where the design pattern rule is 0.3 µm, the detection sensitivity of around 0.1 µm is required on standard. Such defect inspection sensitivity and the number of pixels of the imaging data can be adjusted to some extent at each point within the pattern formation surface.

Figure 3:
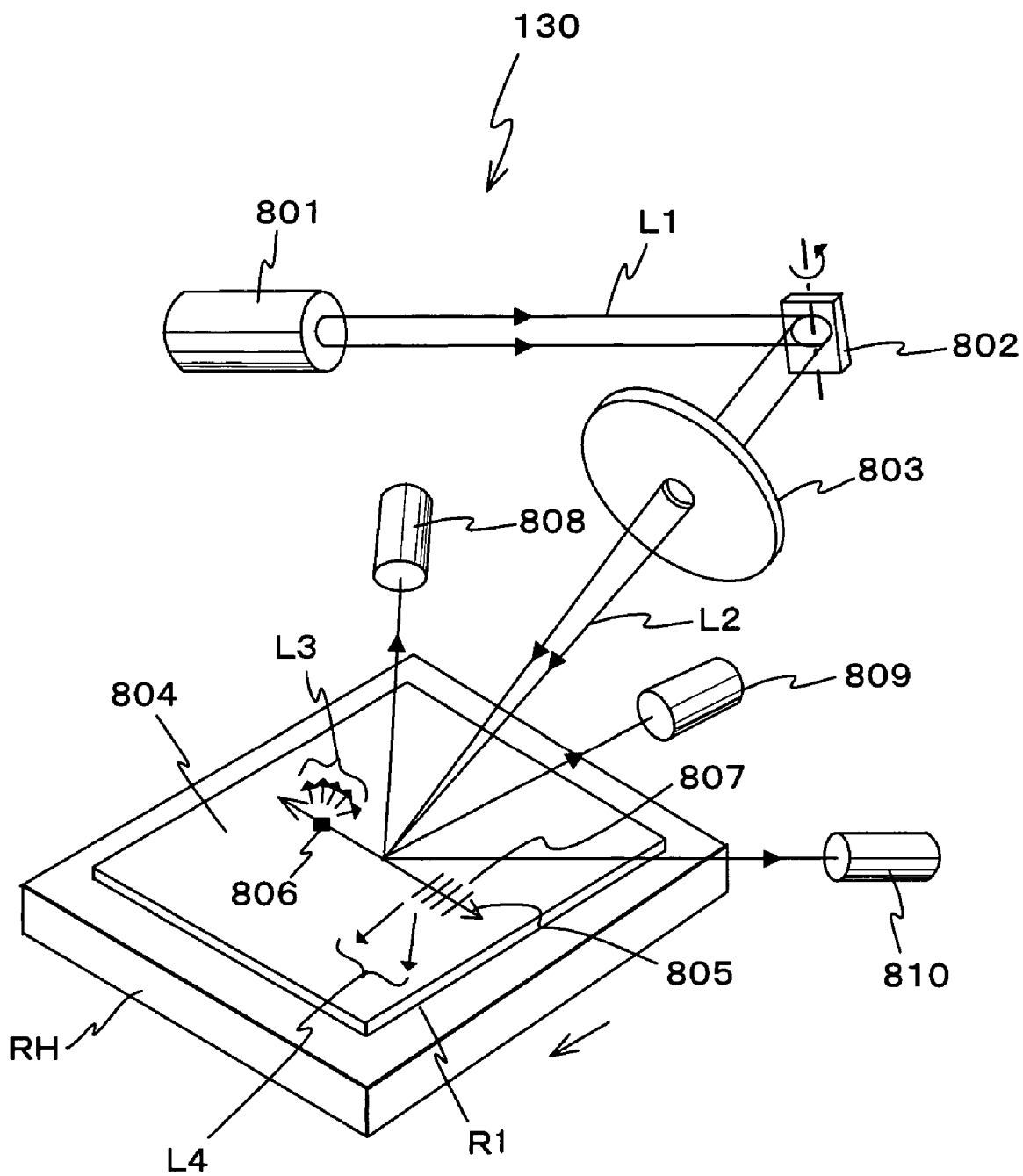
FIG. 3 is a configuration diagram of a reticle measuring and/or inspecting instrument.

Since it is difficult to detect the defects on the light-shielding section of the pattern formation surface in the transmitting illumination method as described above, the defects on the light-shielding section are detected using the laser scattered light method. As is shown in FIG. 3, reticle measuring and/or inspecting instrument 130 includes a stage (not shown) that corresponds to reticle stage RST in exposure apparatus 100, a light source 801, a vibrating mirror 802, a scanning lens 803, photodetectors 808, 809 and 810. Similar to reticle stage RST, the stage is configured capable of holding reticle holder RH, which holds reticle R1, by vacuum suction. On the stage, reticle holder RH is loaded by the reticle holder exchanger described above, and reticle holder RH is held on the stage by suction. Then, on reticle holder RH, reticle R1 is held by suction so that the pattern formation surface faces upward (i.e. two sides of reticle R1 is located in an opposite direction to the case when reticle R1 is held on reticle stage RST). It is assumed that a circuit pattern is formed on the pattern formation surface (a surface to be inspected 804) of reticle R1 and a foreign particle 806 adheres to part of the surface. Although omitted in FIG. 3, a reticle holder that can hold reticle R2 is also arranged on the stage (not shown).

A light beam L1 emitted from light source 801 is polarized by vibrating mirror 802 (a galvano scanner mirror or a polygon scanner mirror) and is incident on scanning lens 803. A light beam L2 emitted from scanning lens 803 performs scanning on a scanning line 805 on surface to be inspected 804. When performing this operation, it becomes possible to scan the entire surface of surface to be inspected 804 with light beam L2, by moving surface to be inspected 804 in a direction orthogonal to scanning line 805 at a speed lower than a scanning period of light beam L2. In this case, when light beam L2 is irradiated to an area in which foreign particle 806 exits on surface to be inspected 804, scattered lights L3 are generated. Further, when light beam L2 is irradiated to an area in which a substance other than a foreign particle adhering on surface to be inspected 804 or a pattern defect exists, for example, a circuit pattern 807 on reticle R1 exists, diffracted lights L4 are generated from pattern 807.

In FIG. 3, photodetectors 808, 809 and 810 are placed so as to face scanning line 805 from directions different from one another. Scattered lights L3 generated from foreign particle 806 become isotropic scattered lights generated toward the substantially all directions. On the other hand, diffracted lights L4 generated from pattern 807 become lights having high directivity that are emitted in spatially discrete directions, because they are generated due to diffraction. By using the differences in characteristics of scattered lights L3 and diffracted lights L4, the judgment can be made that the lights are scattered lights from the defect in the case where all of photodetectors 808, 809 and 810 have detected lights, and the judgment can be made that the lights are the diffracted lights from the pattern in the case where at least one of photodetectors 808, 809 and 810 does not detect lights. As a consequence, reticle measuring and/or inspecting instrument 130 can detect foreign particle 806 on the light-shielding section.

In reticle measuring and/or inspecting instrument 130, the scanning speed of light beam and the moving speed for moving reticle R1 can be changed during scanning. Thus, the scanning speed of light and the moving speed for moving reticle R1 can also be set slightly lower at the place where the defect inspection should be precisely performed. Further, in reticle measuring and/or inspecting instrument 130, the detection sensitivity of scattered lights can be changed during scanning. Thus, the detection sensitivity can be set slightly higher at the place where fine defects should be detected (e.g. the place where a pattern is fine).

Furthermore, reticle measuring and/or inspecting instrument 130 is equipped with a Fizeau interferometer (not shown). Reticle measuring and/or inspecting instrument 130 can measure a surface shape of the pattern formation surface of reticles R1 and R2 in a state of being held on reticle holder RH by suction, using the Fizeau interferometer or the like.

Measurement raw data such as defect inspection data of the pattern formation surface and measurement data of surface shape are stored in a storage unit (not shown). Reticle measuring and/or inspecting instrument 130 is connected to an outside communication network so that data can be sent to and received from the outside apparatuses, and reticle measuring and/or inspecting instrument 130 transmits the measurement raw data, as needed.

Incidentally, in device manufacturing system 1000, a plurality of reticles on which the same patterns are formed are prepared. That is, a plurality of reticles that can be used as reticle R1 and a plurality of reticles that can be used as reticle R2 are prepared. In exposure apparatus 100, reticles having pattern formation surfaces whose suitability for each other are favorable are selected from among the plurality of reticles, and exposure is performed.

[Track]

Track 200 is placed so as to be in contact with a chamber (not shown) that encloses exposure apparatus 100. Track 200 performs carrying-out and carrying-in of wafer W mainly from/to exposure apparatus 100 by a carrier line that is equipped inside track 200.

[Coater Developer]

Within track 200, a coater-developer (C/D) 110 that performs resist coating and development is arranged. The processing state of C/D 110 can be adjusted to some extent by setting its apparatus parameters. As a consequence, a film thickness of resist coated on wafer W, the development time and the like can be adjusted.

C/D 110 can operate independently from exposure apparatus 100 and a wafer measuring and/or inspecting instrument 120. C/D 110 is placed along the carrier line of track 200. Accordingly, the carrier line makes it possible to carry wafer W between exposure apparatus 100 and C/D 110. Further, C/D 110 is connected to the communication network within device manufacturing system 1000 so that data can be sent to and received from the outside. C/D 110 can output, for example, information on the process (information on trace data and the like).

[Wafer Measuring and/or Inspecting Instrument]

Within track 200, composite wafer measuring and/or inspecting instrument 120, which can perform various kinds of measurement and/or inspection to wafer W before and after (i.e. anterior and posterior) exposure of the wafer W in exposure apparatus 100, is arranged. Wafer measuring and/or inspecting instrument 120 can operate independently from exposure apparatus 100 and C/D 110. Wafer measuring and/or inspecting instrument 120 performs anterior measurement and/or inspection processing before exposure and posterior measurement and/or inspection processing after exposure.

In the anterior measurement and/or inspection processing, measurement of surface shape of the surface to be exposed of wafer W, inspection of foreign particles on wafer W, inspection of a resist film on wafer W and the like are performed before wafer W is carried to exposure apparatus 100. Meanwhile, in the posterior measurement and/or inspection processing, measurement of errors in a line width and the overlay of a resist pattern and the like on wafer W after exposure (i.e. posterior) that has been transferred in exposure apparatus 100 and developed in C/D 110, and inspection of wafer defects and foreign particles, and the like are performed. Wafer measuring and/or inspecting instrument 120 can output results of the anterior measurement and/or inspection as data to the outside via the communication network within the system.

Wafer measuring and/or inspecting instrument 120 is placed along the carrier line of track 200. Accordingly, the carrier line makes it possible to carry wafer W among exposure apparatus 100, C/D 110 and wafer measuring and/or inspecting instrument 120. That is, exposure apparatus 100, track 200 and wafer measuring and/or inspecting instrument 120 are inline connected to one another. Herein, the inline connection means the connection between the apparatuses, and between processing units within each apparatus via a carrier unit for performing automating transport of wafer W such as a robot arm or a slider. With the inline connection, a period of time required for delivery of wafer W among exposure apparatus 100, C/D 110 and wafer measuring and/or inspecting instrument 120 can be remarkably shortened.

Exposure apparatus 100, C/D 110 and wafer measuring and/or inspecting instrument 120 that are inline connected, and reticle measuring and/or inspecting instrument 130 can be considered as one substrate processing apparatus (100, 110, 120, 130) as a unit. The substrate processing apparatus (100, 110, 120, 130) performs a measurement and/or inspection process to reticles R1 and R2, a coating process of coating photosensitive agent such as photoresist to wafer W, an exposure process of projecting and exposing images of patterns of reticles R1 and R2 on wafer W whose surface is coated with photosensitive agent, a development process of developing wafer W after the exposure process, and the like. These processes will be described in detail later.

In device manufacturing system 1000, exposure apparatus 100, C/D 100, wafer measuring and/or inspecting instrument 120 and reticle measuring and/or inspecting instrument 130 are (i.e. the substrate processing apparatus (100, 110, 120, 130) is) arranged in plural. Each substrate processing apparatus (100, 110, 120, 130) and device manufacturing apparatus group 900 are installed in a clean room where the temperature and the humidity are controlled. Further, data communication can be performed between the apparatuses via a predetermined communication network (e.g. LAN: Local Area Network). This communication network is a communication network that is a so-called intranet arranged with respect to the plants, offices or business establishments of a client.

In the substrate processing apparatus (100, 110, 120, 130), a plurality of wafers W (e.g. 25 wafers) are processed as one unit (which is called a lot). In device manufacturing system 1000, wafers W in a lot as a basic unit are processed and commercialized. Accordingly, the wafer process in device manufacturing system 1000 is also called the lot processing.

Incidentally, although in device manufacturing system 1000, wafer measuring and/or inspecting instrument 120 is placed within track 200 and inline connected to exposure apparatus 100 and C/D 110, the configuration may also be employed in which they are placed outside track 200 and are set offline with respect to exposure apparatus 100 and C/D 110. Further, reticle measuring and/or inspecting instrument 130 may also be placed within exposure apparatus 100 or track 200. That is, inspection and/or measurement of reticles R1 and R2 may also be performed within exposure apparatus 100. The point is that reticle measuring and/or inspecting instrument 130 should be placed on the carrier route of reticles R1 and R2.

As hardware that realizes the above-described information processing in wafer measuring and/or inspecting instrument 120 and reticle measuring and/or inspecting instrument 130, for example, a personal computer (hereinafter, also referred to as PC) can be employed. In this case, the information processing is realized by execution of a program that is executed by a CPU (not shown) of this information processor. The program is supplied by media (information recording medium) such as a CD-ROM, and is executed in a state of being installed on the PC.

[Analytical Apparatus]

Analytical apparatus 500 is an apparatus that operates independently from exposure apparatus 100 and track 200. Analytical apparatus 500 is connected to the communication network within device manufacturing system 1000 and can send/receive data to/from the outside. Analytical apparatus 500 collects various types of data from various apparatuses (e.g. processing contents of the apparatuses) via the communication network, and performs analysis of data related to processes to wafer W. As hardware to realize such analytical apparatus 500, for example, a personal computer can be employed. In this case, the analytical processing is realized by the execution of an analytical program that is executed by a CPU (not shown) of analytical apparatus 500. The analytical program is supplied by media (information recording medium) such as a CD-ROM and executed in a state of being installed on the PC.

Analytical apparatus 500 performs optimization of processing conditions of reticles R1 and R2 based on measurement and/or inspection results of reticle measuring and/or inspecting instrument 130. Herein, the functions themselves of analytical apparatus 500 may also be included in reticle measuring and/or inspecting instrument 130 or exposure apparatus 100.

[Device Manufacturing Apparatus Group]

As device manufacturing apparatus group 900, a CVD (Chemical Vapor Deposition) apparatus 910, an etching apparatus 920, a CMP (Chemical Mechanical Polishing) apparatus 930 and oxidation/ion-implantation apparatus 940 are arranged. CVD apparatus 910 is an apparatus that forms a thin film on a wafer, etching apparatus 920 is an apparatus that performs etching to a developed wafer. CMP apparatus 930 is a polishing apparatus that planarizes the surface of the wafer by chemical mechanical polishing, and oxidation/ion-implantation apparatus 940 is an apparatus for forming an oxide film on the surface of wafer W or implanting impurities in a predetermined position on wafer W. Further, CVD apparatus 910, etching apparatus 920, CMP apparatus 930 and oxidation/ion-implantation apparatus 940 are also arranged in plural, similar to exposure apparatus 100 and the like, and the carrier routes in which wafer W can be carried among these apparatuses are arranged. Besides the apparatuses described above, device manufacturing apparatus group 900 also includes apparatuses that performs a probing processing, a repair processing, a dicing processing, a packaging processing, a bonding processing and the like.

[Management Controller]

Management controller 160 intensively performs management of an exposure process that is implemented by exposure apparatus 100, and also performs management of C/D 110 and wafer measuring and/or inspecting instrument 120 within track 200 and control of their cooperative operation. As such a controller, for example, a personal computer can be employed. Management controller 160 receives information that shows the progress of processings and operations, and information that shows processing results, measurement and/or inspection results from each apparatus through the communication network within device manufacturing system 1000, grasps the status of the entire manufacturing line of device manufacturing system 1000, and performs management and control of each apparatus so that the exposure process and the like are appropriately performed.

[Host System]

Host system (hereinafter, referred to as a "host") 600 is a main host computer that performs the overall management of entire device manufacturing system 1000, and performs the overall control of exposure apparatus 100, track 200, wafer measuring and/or inspecting instrument 120, reticle measuring and/or inspecting instrument 130 and device manufacturing apparatus group 900. For example, a personal computer or the like can be employed also as host 600. A wired or wireless communication network connects host 600 and other apparatuses, and data communication can be performed between them. With this data communication, host 600 realizes the overall control of this system.

[Device Manufacturing Process]

Figure 4:
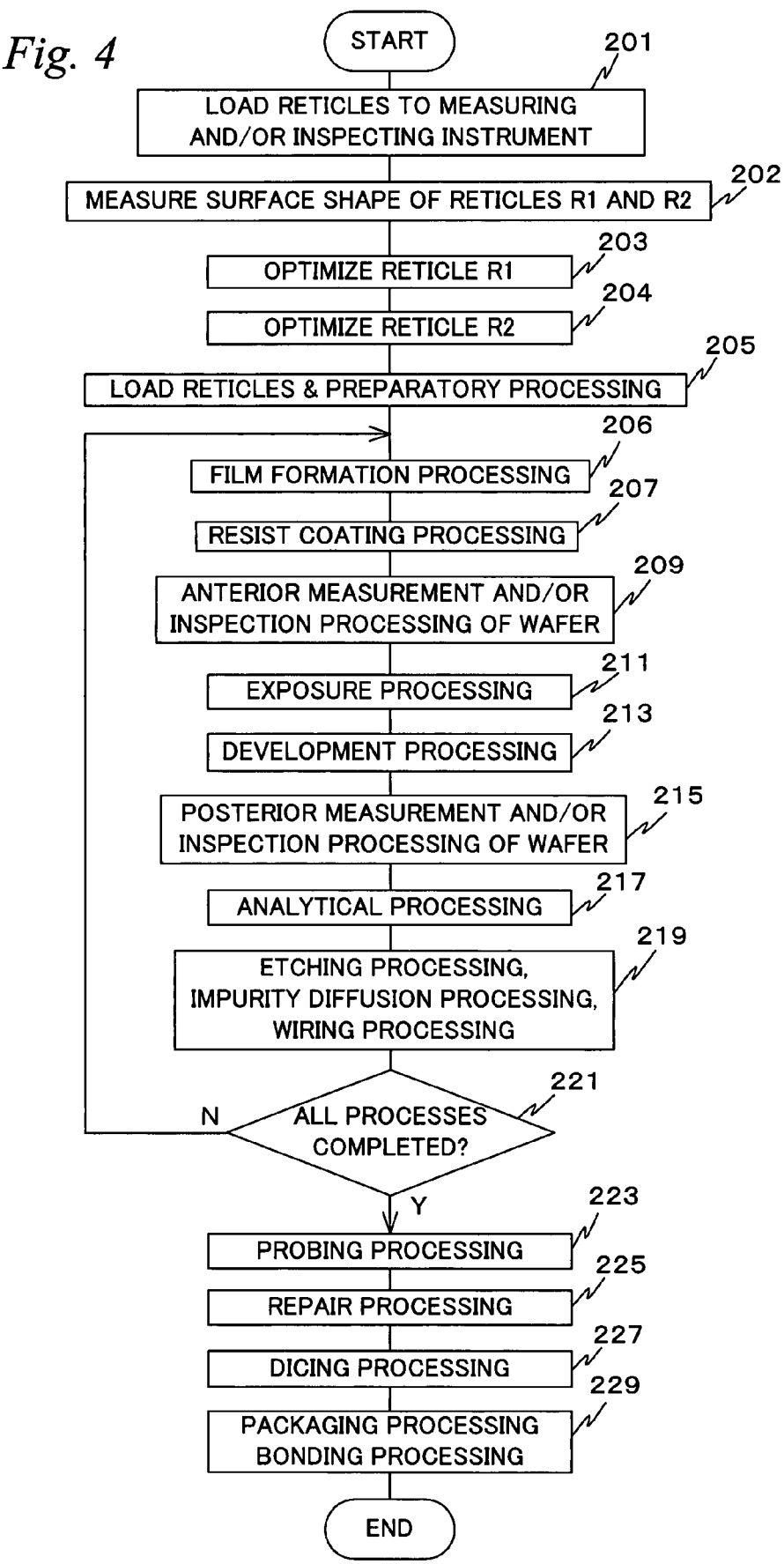
FIG. 4 is a flowchart of a device manufacturing process.

Next, a flow of a series of processes in device manufacturing system 1000 will be described. FIG. 4 shows a flowchart of the processes. The series of processes of device manufacturing system 1000 is scheduled and controlled by host 600 and management controller 160.

First of all, in step 201 in FIG. 4, reticles R1 and R2 are loaded into reticle measuring and/or inspecting instrument 130. On the stage of reticle measuring and/or inspecting instrument 130, two reticle holders RH are held by suction and reticles R1 and R2 are each held by suction in the orientation described earlier by reticle holder RH.

In the next step, step 202, the surface shapes of pattern formation surfaces of reticles R1 and R2 are each measured. The surface shape data is sent to analytical apparatus 500.

In the next step, step 203, reticle R1 is optimized. In this step, a defect inspection of the pattern formation surface of reticle R1 in reticle measuring and/or inspecting instrument 130 and optimization of reticle R1 in analytical apparatus 500 using the inspection results are performed.

Figure 5:
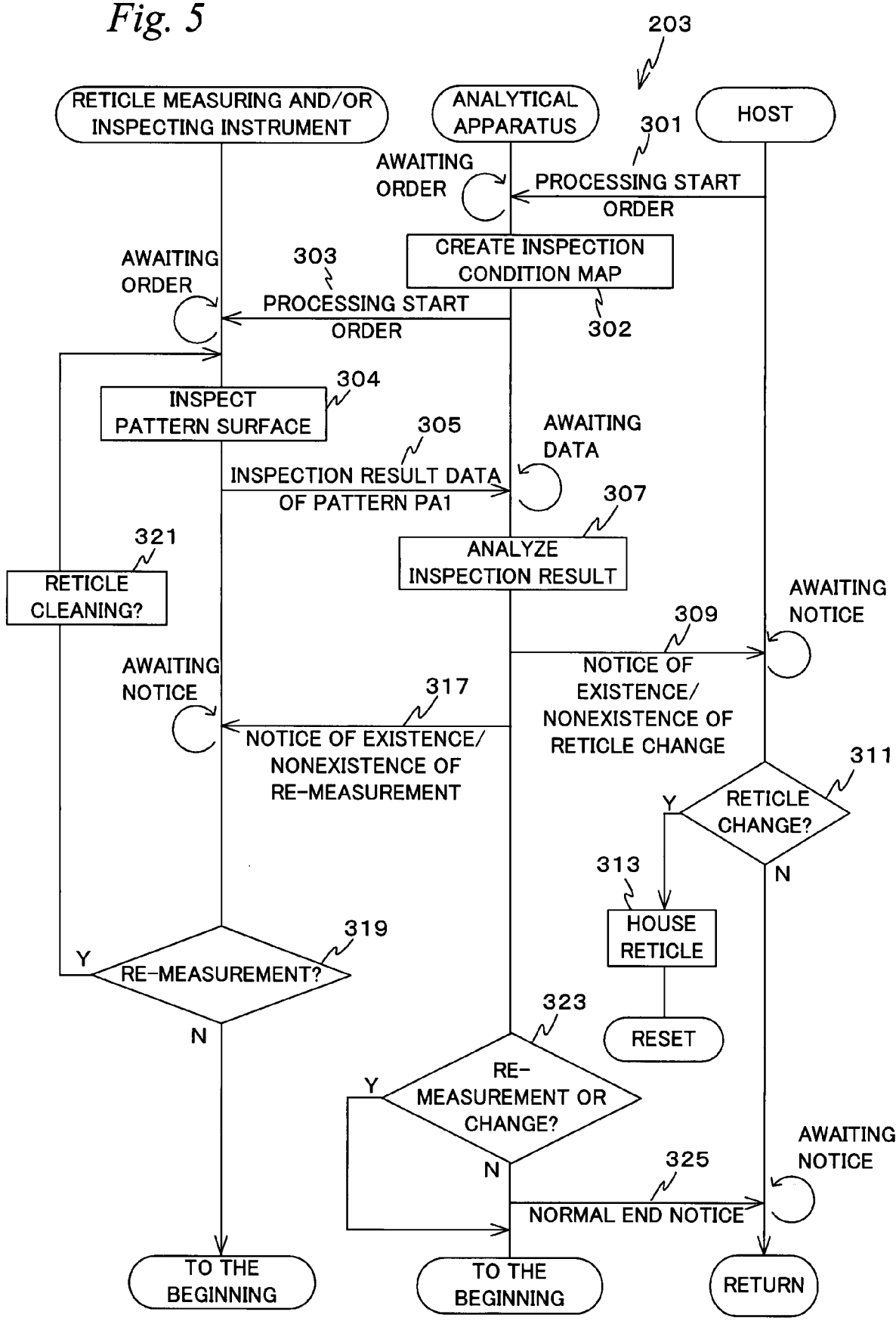
FIG. 5 is a flowchart of reticle optimization.

FIG. 5 shows a flow diagram of the optimization of reticle R1 performed in step 203. As is shown in FIG. 5, in step 301, host 600 issues a processing start order to analytical apparatus 500. When analytical apparatus 500, which has been awaiting the order, receives the order, the procedure proceeds to step 302. In step 302, analytical apparatus 500 creates an inspection condition map used when performing the defect inspection of reticle R1 of reticle measuring and/or inspecting instrument 130. In reticle measuring and/or inspecting instrument 130, the inspection condition can be changed according to each area of the pattern formation surface of reticle R1. The inspection condition map shows the inspection conditions, which are used to detect only defects that directly affect the yield of device production in the defect inspection of reticle R1, being linked with places within the pattern formation surface.

The criteria for creating the inspection condition map is mainly based on the attribute of a pattern formed on the place. For example, first, the inspection condition of reticle R1 can be changed depending on whether a certain point within the pattern area of reticle R1 is the light-transmitting section or the light-shielding section. In the embodiment, the defects of the light-transmitting section affect a transfer result of wafer W more easily than those of the light-shielding section, and therefore it is preferable to change the inspection condition so that the defects of the light-transmitting section are detected more rigorously. Analytical apparatus 500 extracts an arbitrary point within a pattern area (which is to be PA1) of reticle R1, and classifies the point according to the attribute of the point, that is, whether the point is the light-transmitting section or the light-shielding section (this attribute is to be a first attribute of pattern area PA1).

Further, in the embodiment, the inspection condition of pattern area PA1 of reticle R1 can be changed according to a pattern area (PA2) of counterpart reticle R2. Analytical apparatus 500 further divides pattern area PA1, by classifying the point according to the attribute of whether a point in pattern area PA2 of reticle R2 corresponding to the point in pattern area PA1 is the light-transmitting section or the light-shielding section (this attribute is to be a first attribute of pattern area PA2), the attribute of whether or not the point is located in a proximity area to the pattern (this attribute is to be a second attribute of pattern area PA2), and the attribute regarding a type of the pattern that is proximate (this attribute is to be a third attribute of pattern area PA2).

Rules that are applied when performing this classification will be described.

Figure 6A:
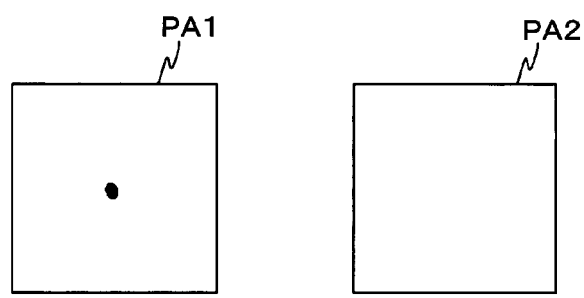
FIGS. 6A to 6E are views for explaining classification of pattern areas.

(1) FIG. 6A shows an area having the attribute (the first attribute) of pattern area PA1 of reticle R1 that is the light-transmitting section, the first attribute of pattern area PA2 of reticle R2 that is the light-transmitting section, and the second attribute that is an area other than the proximity area. Concerning such an area, even if a fine foreign particle (refer to FIG. 6A) adheres to the area of reticle R1, a portion that has not been exposed due to existence of the foreign particle is exposed by an exposure light that is transmitted through the light-transmitting section of a counterpart reticle (reticle R2, in this case), and therefore, the influence of the foreign particle that affects the actual exposure result on wafer W can be considered to be relatively small. Thus, with regard to such a portion, for example, a permissible size of a foreign particle to be detected is preferably set larger than a standard size.

In the multiple exposure, however, the exposure dose of exposure lights IL1 and IL2 is set under the assumption that the portion is the light-transmitting section of both reticles R1 and R2, and in the case where the total of the entire exposure dose is reduced to the level that cannot be ignored due to the foreign particle, some measures against the foreign particle needs to be taken. Also in this regard, the permissible size of a foreign particle needs to be appropriately set, taking the entire exposure dose into consideration.

Figure 6B:
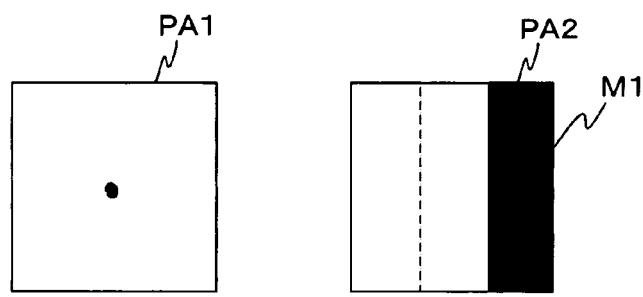

(2) In the case where the first attribute of a portion in pattern area PA1 of reticle R1 is the light-transmitting section, the first attribute of a portion in pattern area PA2 of reticle R2 that corresponds to the portion in pattern area PA1 is the light-transmitting section, the second attribute is the proximity area, and the third attribute of the portion is a conventional pattern, if a foreign particle adheres to the portion, the influence of the foreign particle on the transfer result of wafer W is synergistically increased due to optical proximity effect and the like, and therefore, the defects in this portion (area) need to be detected with high sensitivity. Herein, such an area is classified into an area B. FIG. 6B shows the status in which the foreign particle adhering onto pattern area PA1 corresponds to the proximity area to a conventional pattern M1 on pattern area PA2. In area B, the foreign particles are detected with high sensitivity.

Figure 6C:
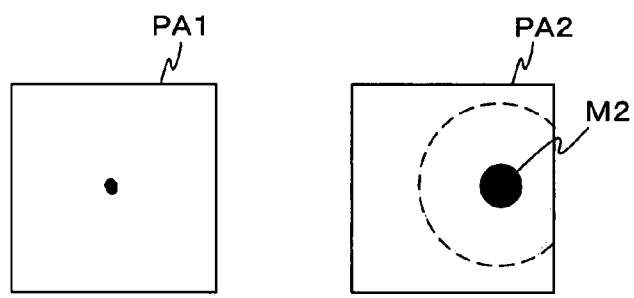

(3) An area having the first attribute of pattern area PA1 of reticle R1 that is the light-transmitting section, the first attribute of pattern area PA2 of reticle R2 that is the light-transmitting section, the second attribute that is the proximity area to the pattern, and the third attribute that is a contact hole pattern is classified into an area C. FIG. 6C shows the status in which a foreign particle adhering onto pattern area PA1 corresponds to the proximity area (indicated by a dotted line) to a contact hole pattern M2 on pattern area PA2. With regard to also area C as described above, the detection sensitivity is preferably set high.

Figure 6D:
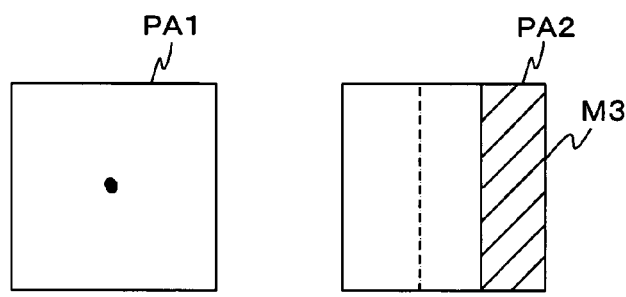

(4) An area having the first attribute of pattern area PA1 of reticle R1 that is the light-transmitting section, the first attribute of pattern area PA2 of reticle R2 that is the light-transmitting section, the second attribute that is the proximity area to the pattern (an area on the right side of the dotted line in FIG. 6D), and the third attribute that is a phase shift pattern is classified into an area D. FIG. 6D shows the status in which a foreign particle adhering onto pattern area PA1 exists in an area that corresponds to the proximity area to a phase shift pattern M3 on pattern area PA2, that is, exists in area D. The detection sensitivity of area D as described above is also preferably set to high sensitivity.

Figure 6E:
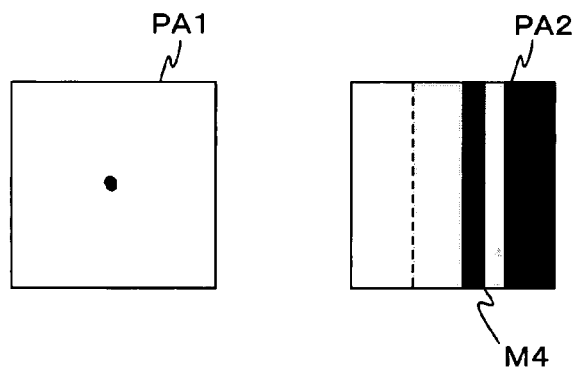

(5) In the case where a portion (an area) has the first attribute of pattern area PA1 of reticle R1 that is the light-transmitting section, the first attribute of pattern area PA2 of reticle R2 that is the light-transmitting section, the second attribute that is the proximity area to the pattern, and the third attribute that is an OPC (Optical Proximity Correction) pattern, the area is classified into an area E. FIG. 6E shows the status in which a foreign particle adhering onto pattern area PA1 exists in an area that corresponds to the proximity area to an OPC pattern M4 (an area on the right side of the dotted line) on pattern area PA2. The detection sensitivity of area E as described above is also preferably set high.

(6) In the case where a portion (an area) has the first attribute of pattern area PA1 of reticle R1 that is the light-transmitting section, and the first attribute of pattern area PA2 of reticle R2 that is the light-shielding section, the area is classified into an area F. If a foreign particle adheres to area F, the influence on the exposure result of wafer W is large, and therefore, the permissible size of a foreign particle is set slightly smaller than the standard size.

(7) An area that has the first attribute of pattern area PA1 of reticle R1 being the light-shielding section is classified into an area G. Even if a foreign particle adheres to area G, the foreign particle does not directly affect the exposure result of wafer W. In particular, a submicron foreign particle generally adheres to the surface firmly, and is not moved by the gravity, vibration, shock and air blowing. However, since it is possible for a relatively larger (e.g. a micron unit) foreign particle to move to the light-transmitting section during reticle carriage, such a foreign particle needs to be removed beforehand. Thus, in area G described above, the permissible size of a foreign particle is preferably set slightly larger.

FIG. 7 shows a table in which the rules of the above (1) to (7) are described. Incidentally, the detection sensitivity for areas B to E and the permissible size for areas A, F and G can be set independently, and can be individually changed according to a size of the proximity pattern.

Further, analytical apparatus 500 computes the difference in the flatness degree between pattern area PA1 and pattern area PA2 based on the surface shape data of reticles R1 and R2 obtained in step 202. Then, for an area in which the difference in the flatness degree exceeds a predetermined value, the inspection data sampling resolution is set high so that precise inspection can be performed. Herein, the inspection data sampling resolution can be adjusted by changing setting of the number of pixels (imaging magnification) and the like for the area in the case of inspection by imaging, or can be adjusted by the scanning speed of a laser light and/or the moving speed of a reticle and the like in the case of inspection by laser scanning.

Analytical apparatus 500 sends a processing start order that includes data related to this inspection condition map to reticle inspecting and/or measuring instrument 130 (step 303). When reticle inspecting and/or measuring instrument 130, which has been awaiting the order, receives the order, the procedure proceeds to step 304. In step 304, reticle inspecting and/or measuring instrument 130 inspects the pattern formation surface of reticle R1.

In the inspection of the pattern formation surface of reticle R1, a defect inspection is performed under the inspection conditions according to the inspection condition map created in step 302. As is described above, in the inspection condition map, pattern area PA1 of reticle R1 is classified into areas A to G, and the defect inspection of pattern area PA1 is performed while changing the inspection conditions, that is, the inspection sensitivity, the inspection data sampling resolution, the permissible size of a foreign particle and the like. In this case, inspection data of the light-shielding section in pattern area PA1 of reticle R1 and pattern area PA2 of reticle R2 is acquired using the laser scattered light method, and inspection data of the light-transmitting section in pattern area PA1 of reticle R1 and pattern area PA2 of reticle R2 is acquired using the imaging method by transmitted light.

Then, in the next step, step 305, reticle inspecting and/or measuring instrument 130 sends data of defect inspection results to analytical apparatus 500. When analytical apparatus 500, which has been awaiting the defect inspection data, receives the data, the procedure proceeds to step 307. In step 307, analytical apparatus 500 performs analysis of the inspection results. Analytical apparatus 500 analyzes the data of defect inspection results to analyzes the existence/nonexistence and position coordinates of hard defects and soft defects within the pattern formation surface of reticle R1, and the like. Then, analytical apparatus 500 sets a mode for changing the reticle if the hard defect exists, and sets a mode for cleaning reticle R1 if the soft defect exists.

In the next step 309, analytical apparatus 500 notifies the existence/nonexistence of reticle change to host 600. When host 600, which has been awaiting the notice, receives the notice, the procedure proceeds to step 311. In step 311, whether or not the reticle change is necessary is judged, and in the case where the hard defect exists and the judgment is affirmed, the procedure proceeds to step 313, in which reticle R1 and/or reticle R2 having the hard defect is housed, and a processing for a reticle that is replaced is reset. When the reset is performed, the processing is re-started from step 201 using two reticles that have been newly selected as reticles R1 and R2. On the other hand, in the case where the judgment is made in step 311 that the reticle change is not necessary, host 600 becomes again in a state of awaiting a notice.

Meanwhile, the procedure proceeds from step 309 to step 317, and analytical apparatus 500 notifies the existence/nonexistence of adjustment of reticle R1 to reticle measuring and/or inspecting instrument 130. When reticle measuring and/or inspecting instrument 130, which has been awaiting the notice, receives the notice, the procedure proceeds to step 319. In step 319, reticle measuring and/or inspecting instrument 130 judges whether or not adjustment of reticle R1 is necessary. When the adjustment is judged to be necessary, the judgment is affirmed, and the procedure proceeds to step 321, in which cleaning of the reticle is performed in order to remove the soft defect.

After completing the adjustment of reticle R1, again re-inspection of the pattern formation surface of reticles R1 and R2 is performed.

The procedure proceeds to step 323 that is the next step to step 317, and in step 323 analytical apparatus 500 judges whether or not the reticle change is necessary, or the reticle adjustment is necessary. Only in the case where the judgment is denied, the procedure proceeds to step 325, and analytical apparatus 500 notifies the normal end to host 600. After the normal end is notified, or after the judgment is affirmed in step 323, the procedure returns the first step, and again analytical apparatus 500 returns to a state of awaiting the order. Meanwhile, in host 600 that has received the normal end notice, the procedure proceeds to step 204 in FIG. 4.

In step 204, optimization of reticle R2 is performed in the similar manner to step 203 described above. Also in this case, analytical apparatus 500 creates an inspection condition map of the pattern formation surface of reticle R2, and a defect inspection of the pattern formation surface of reticle R2 that is directly related to the yield is performed, according to the inspection condition map. Then, in the case where the hard defect exists, the reticle replacement is performed, and in the case where the soft defect exists, the reticle cleaning is performed.

Incidentally, in the steps 203 and 204 described above, measurement of the transmittance of reticles R1 and R2 is also performed. By the measurement of the transmittance, the entire exposure dose of exposure lights IL1 and IL2 that reach the surface of wafer W can be known.

In the next step, step 205, reticles R1 and R2 held via reticle holder RH on the stage of reticle measuring and/or inspecting instrument 130 are severally loaded on reticle holder RH on reticle stage RST using the reticle exchanger, and the preparatory operation is performed such as alignment of reticles R1 and R2 (reticle alignment) and measurement of baseline (a distance between an off-axis alignment sensor (not shown) and the pattern center of reticles R1 and R2). With this preparatory operation, it becomes possible to overlay a device pattern on the pattern formation surface of reticles R1 and R2 with respect to an arbitrary area on wafer W that is positioned on wafer stage WST. Incidentally, in the case of using reticle measuring and/or inspecting instrument 130 that has the structure with which measurement and/or inspection can be performed in a state where reticles R1 and R2 are each held on reticle holder RH in the orientation similar to the orientation on reticle stage RST, reticle holder RH holding reticle R1 and reticle holder RH holding reticle R2 can be loaded on reticle stage RST.

After that, the processing to wafer W is performed. First of all, a film is formed on the wafer in CVD apparatus 910 (step 206), the wafer W is carried to C/D 110, in which resist is coated on the wafer (step 207). Herein, in C/D 110, types, film thickness and the like of the resist to be coated on wafer W can be adjusted in accordance with the total of the transmittance of reticles R1 and R2, which have been measured in advance in steps 203 and 204, under instructions from analytical apparatus 500 or host 600.

Next, wafer W is carried to wafer measuring and/or inspecting instrument 120, in which anterior measurement and/or inspection processing such as measurement of the surface shape of wafer W and inspection of foreign particles on the wafer is performed (step 209). The measurement results (i.e. data related to the surface shape and the like) of wafer measuring and/or inspecting instrument 120 are sent to exposure apparatus 100 and analytical apparatus 500. The measurement results are used for focus control at the time of scanning exposure in exposure apparatus 100.

Subsequently, the wafer is carried to exposure apparatus 100, and the exposure processing in which circuit patterns on reticles R1 and R2 are transferred onto wafer W is performed in exposure apparatus 100 (step 211).

In exposure apparatus 100, feedback control is performed in which the patterns within illumination areas IAR1 and IAR2 are projected to exposure area IA and the surface to be exposed of wafer W is located within the depth of focus of projection optical system PL, in a state where the states of exposure dose, synchronous accuracy, focus and lens follow the target values by an exposure dose control system, a stage control system and a lens control system. In this scanning exposure, in the case where the patterns of reticles R1 and R2 are device patterns of a plurality of chips, a chip area corresponding to an abnormal place may be blinded by illumination system 10, and the exposure processing may be performed only to normal chip areas.

Next, wafer W is carried to C/D 110, in which development processing is performed (step 213). In this development processing, the development time of wafer W can be adjusted in accordance with the total of exposure doses that are predicted from the transmittance of reticles R1 and R2. That is, in the case where the total of exposure doses is less than a predetermined value, the development time may be set longer. After that, the posterior measurement and/or inspection processing is performed such as measurement of a line width of a resist image, line width measurement of device patterns transferred onto wafer W and pattern defect inspection (step 215).

Data related to the measurement and/or inspection results is sent to analytical apparatus 500. In the next step, step 217, analytical apparatus 500 performs analysis of the measurement and/or inspection results. Analytical apparatus 500 confirms whether or not the device pattern transferred and formed on wafer W have defects, judges whether there is the correlation between the defects and the defect inspection of reticles R1 and R2, and in the case where the correlation is recognized, the detection sensitivity, the permissible size of a foreign particle and the like are adjusted that have been set in advance for creating the inspection condition map used to detect the hard defects and soft defects on reticles R1 and R2.

Wafer W is carried from wafer measuring and/or inspecting instrument 120 to etching apparatus 920, in which etching is performed, and impurity diffusion, wiring processing, film formation in CVD apparatus 910, planarization in CMP apparatus 930, ion-implantation in oxidation/ion-implantation apparatus 940, and the like are performed as needed (step 219). Also in the etching, the etching time of wafer W can be adjusted in accordance with the total of the transmittance of reticles R1 and R2.

Then, in host 600, the judgment is made of whether or not all the processes have been completed and all the patterns have been formed on the wafer (step 221). When the judgment is denied, the procedure returns to step 206, and when the judgment is affirmed, the procedure proceeds to step 223. Circuit patterns are layered on wafer W and a semiconductor device is formed, by repeatedly executing a series of processes such as film formation/resist coating to etching according to the number of processes, as is described above.

After completing repeated processes, probing processing (step 223) and repair processing (step 225) are executed in device manufacturing apparatus group 900. When a memory defect is detected in step 223, for example, processing for replacing it with a redundant circuit is performed in step 225. In an inspecting unit (not shown), the place where a linewidth abnormality occurs on wafer W can be excluded chip by chip from the subject to proving processing and repair processing. Afterward, dicing processing (step 227), packaging processing and bonding processing (step 229) are executed, and a product chip is finally completed. Incidentally, the posterior measurement and/or inspection processing of the wafer in step 215 may also be performed after the etching in step 219. In this case, linewidth measurement is performed to an etching image on wafer W. Or, linewidth measurement may also be performed after the development and also after the etching. In this case, linewidth measurement is performed to both a resist image and an etching image, and therefore it becomes possible to detect a processing state of the etching processing based on the difference between measurement results.

As is described so far in detail, according to the embodiment, since a defect inspection of one of reticles that are used for exposure to the same area on wafer W is performed taking information on the other of reticles into consideration, the defect inspection of reticles R1 and R2 directly related to the yield of device production, in which not only an exposure state individually using reticles R1 and R2 but also a comprehensive state of actual exposure onto wafer W are taken into consideration, can be performed.

Further, in the embodiment, the actual transfer result of a pattern on wafer W is measured and/or inspected (step 215), and based on the measurement and/or inspection results, the inspection contents of reticle measuring and/or inspecting instrument 130 are adjusted. That is, the judgment is made of whether there is the correlation between the transfer result of wafer W and the defect inspections of reticles R1 and R2 that are performed in steps 202, 203 and 204, and in the case where abnormality of the transfer result of wafer W is caused by the pattern of reticles R1 and R2, the inspection sensitivity and a threshold value (i.e. inspection conditions indicated in the inspection condition map) and the like in the defect inspection are adjusted. With this operation, the inspection conditions can be optimized so that only defects that actually affect the yield are detected. Especially, the more the pattern on the reticle become complicated, such as an OPC pattern or a phase shift pattern existing within the pattern area of reticle R1 or R2, the more it becomes important to reflect the exposure results in the inspection conditions.

Further, in the embodiment, since it can be considered that the defect of the light-transmitting section more profoundly affects the yield of devices than the defect of the light-shielding section in the defect inspection of reticles R1 and R2, the light-transmitting section is more precisely inspected. With this operation, the defect inspection in which only defects that affect the yield of device production are detected can be performed.

Further, according to the embodiment, in the defect inspection related to one of reticles R1 and R2, the processing contents of the defect inspection are changed by changing the detection sensitivity and the permissible size of a foreign particle and the like, in accordance with whether the light-transmitting section of the pattern is formed or the light-shielding section of the pattern is formed at a position on the other reticle corresponding to a specific position of the light-transmitting section of the pattern area of one reticle. This makes it possible to inspect more rigorously a portion that more affects the exposure result of wafer W, and therefore the defect inspection by which only defects that affects the yield of device production are detected can be performed.

Further, in the embodiment, in the defect inspection of one of reticles R1 and R2, the inspection condition map is created in accordance with information on the pattern on the other reticle, and the detection sensitivity of defects is controlled. For example, the defect that exists at a portion, which is the light-transmitting section on one reticle and which corresponds to a proximity area to a pattern on the other reticle, largely affects the exposure result of wafer W, and accordingly, the detection sensitivity is set high. With this setting, it becomes possible to inspect the portion that largely affects the exposure result of wafer W with higher sensitivity, which makes it possible to perform the defect inspection in which only defects that affect the yield of device production are detected.

Further, according to the embodiment, in the optimization of reticles R1 and R2 (steps 203 and 204), inspection result data of the light-transmitting section is output to analytical apparatus 500 (step 305). Then, the relation between a size of the detected foreign particle and the permissible size is changed in accordance with information on a pattern of the other reticle. With this operation, the permissible size of a foreign particle in a portion that largely affects the exposure result of wafer W can be made to be different from that in a portion that less affects the exposure result, and only the foreign particles that affect the yield of device production can be detected.

Further, according to the embodiment, in accordance with one of the patterns, the inspection data sampling resolution of the other of the patterns is changed. With this operation, a portion that largely affects the exposure result of wafer W can be detected more precisely, which makes it possible to perform the defect inspection in which only defects that affect the yield of device production are detected.

Further, according to the embodiment, a foreign particle adhering to the light-transmitting section of a pattern on a reticle is detected and also a foreign particle adhering to the light-shielding section of the reticle is detected. The foreign particle adhering to the light-shielding section does not directly affect the exposure result of wafer W, but the case is possible where the foreign particle moves to the light-transmitting section during reticle carriage, and therefore the foreign particle is preferably detected if it has a certain level of size.

Further, in the embodiment, in the optimization of reticles R1 and R2 (steps 203 and 204), not only inspection result data of the light-transmitting section but also that of the light-shielding section are output to analytical apparatus 500 (step 305). Then, also in the inspection of the light-shielding section, the output contents are changed in accordance with a size of the detected foreign particle. With this operation, the inspection contents (e.g. the permissible size) of a foreign particle in a portion that largely affects the exposure result of wafer W can be made to be different from those in a portion that less affects the exposure result, and detection of defects that is directly related to the yield of device production can be performed.

Further, according to the embodiment, in accordance with whether or not either of an optical proximity correction pattern, a phase shift pattern or a contact hole pattern is formed in the vicinity of a position on one of reticles R1 and R2 that corresponds to a specific position in a pattern of the other of reticles R1 and R2, the processing contents of the defect inspection related to the specific position in the pattern are changed. With this operation, the inspection contents (e.g. inspection sensitivity) of a foreign particle in a proximity area to each of the patterns referred to above that largely affects the exposure result of wafer W can be made to be different from those in other areas, and detection of defects that is directly related to the yield of device production can be performed.

Incidentally, in the embodiment, the inspection conditions are optimized beforehand based on information of a counterpart reticle, but inspection may also be performed under the uniform inspection conditions, and whether or not the inspected defect is a defect that is directly related to the yield of device production may be judged using information on a counterpart reticle.

Further, in the embodiment, in accordance with the difference in surface shape between a specific position in a pattern of one of the reticles and a corresponding position on the other of the reticles, the processing contents of the defect inspection related to the specific position in the pattern are changed. With this operation, the inspection contents (e.g. inspection data sampling resolution) of a foreign particle in a portion having the large difference in the flatness degree that profoundly affects the exposure result of wafer W can be made to be different from that of a foreign particle in a portion having the small difference in the flatness degree, and the defect detection that is directly related to the yield of device production can be performed.

Further, in the embodiment, in the case where at least one of a plurality of reticles R1 and R2 placed on the optical path of each of a plurality of exposure lights IL1 and IL2 irradiated to the same area on the surface to be exposed of wafer W is measured and/or inspected, the total dose (total of light quantity) of exposure lights IL1 and IL2 irradiated on the same area on the surface to be exposed of wafer W is obtained. Then, the output contents of measurement and/or inspection results are changed in accordance with the total dose of exposure lights IL1 and IL2. With this operation, the output contents of the measurement and/or inspection results can be made to be different in accordance with the total dose of exposure lights IL1 and IL2, and the measurement and/or inspection that is directly related to the yield of device production can be performed.

Further, in the embodiment, in accordance with information on a pattern formed on reticle R1 that is placed on the optical path of each of exposure lights IL1 and IL2, the exposure processing of wafer W is controlled based on a result of measuring and/or inspecting the other reticle, reticle R2 that is different from reticle R1. With this operation, it becomes possible to control the exposure processing based on information related to all the reticles used for exposure, and thus, exposure with high accuracy and high throughput can be performed and the yield of device production is improved.

Further, in the embodiment, when multiple exposure (double exposure) in which a plurality of exposure lights IL1 and IL2 are irradiated to the surface to be exposed of wafer W is performed, in accordance with information on a pattern formed on one reticle of reticles R1 and R2 that are placed on the optical path of each of a plurality of exposure lights IL1 and IL2, the defect inspection of the other reticle is performed. This makes it possible to perform the defect inspection of the reticle that is directly related to the yield of device production in which not only an exposure sate using the individual reticle but also a comprehensive state of actual exposure onto wafer W are taken into consideration.

Further, according to the embodiment, in the case where a defect of a reticle that affects the yield is detected taking the combination with a counterpart reticle into consideration, if the defect is a soft defect, cleaning of the reticle is performed, or if the defect is a hard defect, exchange of the reticle or the like is performed. This makes it possible to perform appropriate processing to various defects of the reticle and improvement in the yield of device production can be expected.

Incidentally, in the embodiment described above, two reticles used for exposure are both glass reticles, but if either one of reticles R1 and R2 is an electron mask such as a liquid crystal panel that can change a pattern formed thereon, the yield of device production can be further improved.

For example, even if a foreign particle adheres to the light-transmitting section of a glass reticle and a point on an electron mask, which corresponds to a point where the foreign particle exists on the glass reticle, is located in the light-shielding section in design, the light-shielding section can be changed to the light-transmitting section. With this operation, a point on the surface to be exposed of wafer W corresponding to the point where the foreign particle exists is exposed by an exposure light via the electron mask and the cleaning of the reticle becomes unnecessary depending on a size of the foreign particle, which is advantageous in terms of throughput.

Further, in the case where the transmittance of reticles R1 and R2 is low in total, and it is predicted that the total of entire exposure dose is too weak, the same pattern (such as a contact hole pattern or a fine line pattern) as the pattern that has been formed on a pattern area of the glass reticle may also be formed on the electron mask. With this operation, even if the entire exposure dose is too weak, it becomes possible to transfer and form the pattern in a clear state on the surface to be exposed of wafer W.

Incidentally, in the embodiment described above, the pattern area of one reticle and the pattern area of the other reticle are classified into several areas. Then, the defect inspection of the pattern areas is performed while changing the inspection conditions with respect to each classified area. However, the present invention is not limited to this, and in the case where a phenomenon that may questionably be abnormality is detected in either one of the pattern areas, the judgment may be made of whether the detected phenomenon is deemed to be abnormality or deemed not to be abnormality, taking information on the other pattern area into consideration.

Incidentally, in the embodiment described above, analytical apparatus 500 and reticle measuring and/or inspecting instrument 130 are separately equipped, but both of them may also be integrally equipped. That is, reticle measuring and/or inspecting instrument 130 may also have the function of analytical apparatus 500.

Incidentally, a transmissive reticle is used in the embodiment described above, but a reflective reticle may also be used. Further, in the embodiment, two reticles are used in one exposure processing, but one reticle on which two pattern areas are formed may also be used.

Incidentally, in the embodiment, exposure apparatus 100 that projects images of patterns of two reticles R1 and R2 on wafer W via the same projection optical system PL is used, but an exposure apparatus that projects two pattern images on wafer W via separate projection optical systems may also be used.

Further, exposure apparatus 100 related to the embodiment transfers device patterns onto wafer W by simultaneous double exposure of the patterns, but an exposure apparatus that can simultaneously perform triple exposure, quadruple exposure and so forth may also be used as a matter of course. In this case, when the defect inspection of one reticle is performed, information on all of other reticles is preferably taken into consideration.

Further, as exposure apparatus 100 related to the embodiment, an exposure apparatus that performs so-called multiple exposure in which a plurality of patterns are simultaneously exposed is used, but, as a matter of course, the present invention can also be employed in an exposure apparatus that exchanges reticles as needed and performs multiple exposure.

Incidentally, there is no obvious limitation regarding patterns of reticles R1 and R2 in the multiple exposure method related to the embodiment. For example, a pattern within one of pattern areas may be a device pattern in design to be transferred and formed on wafer W, and a pattern within the other of the pattern areas may be an OPC pattern. Moreover, the design can also be employed with which a phase shift effect is realized by making the phase difference between an exposure light via a pattern within one of pattern areas and an exposure light via a pattern within the other of the pattern areas be 180 degrees, and giving the phase difference to the exposure lights via both reticles.

In order to gain the phase shift effect for both reticles, the phase difference of lights via the respective reticles needs to meet the design value (e.g. 180 degrees), and therefore, the phase difference can preferably be measured in the measurement and/or inspection of the reticles. In this case, the phase difference between shifters of individual patterns is measured and/or inspected using a Mach-Zehnder interferometer or the like, and it should be confirmed that the phase difference between the shifters meets the design value.

Incidentally, the types of exposure apparatuses are not limited in the present invention. For example, the present invention can also be applied to an exposure apparatus that is equipped with a wafer stage that holds wafer W and a measurement stage on which a reference member having a reference mark formed thereon and/or various types of photoelectric sensors are mounted, as is disclosed in Kokai (Japanese Unexamined Patent Application Publications) No. 11-135400 and No. 2000-164504, and the like.

Further, in the embodiment described above, the projection exposure apparatus by a step-and-scan method is described. However, it is needless to say that the present invention can also be applied to other exposure apparatuses such as an exposure apparatus by a step-and-repeat method or an exposure apparatus by a proximity method, besides the projection exposure apparatus described above. In addition, the present invention can suitably be applied also to a reduction projection exposure apparatus by a step-and-stitch method that synthesizes a shot area with a shot area. As represented by these exposure apparatuses, the types of the various apparatuses are noted limited.

Further, the present invention can also be applied to a twin-stage type exposure apparatus that is equipped with two wafer stages, as is disclosed in, for example, the pamphlets of International Publications No. 98/24115 and No. 98/40791. Furthermore, it is a matter of course that the present invention can also be applied to an exposure apparatus that uses a liquid immersion method, as is disclosed in, for example, the pamphlet of International Publication No. 99/49504. In this case, an exposure apparatus in which the space between a projection optical system and a substrate is locally filled with liquid is employed, but the present invention can also applied to a liquid immersion exposure apparatus that performs exposure in a state where the entire surface to be exposed of a substrate that is subject to exposure is immersed in liquid, as is disclosed in Kokai (Japanese Unexamined Patent Application Publications) No. 06-124873 and No. 10-303114, the U.S. Pat. No. 5,825,043 and the like.

Further, the present invention can be applied not only the semiconductor manufacturing process but also to a manufacturing process of displays including liquid crystal display devices and the like. Furthermore, besides a process of transferring device patterns onto glass plates, a process of manufacturing thin film magnetic heads, and a process of manufacturing imaging devices (such as CCDs), micromachines, organic EL, DNA chips and the like, the present invention can be applied to all the device manufacturing processes as a matter of course.

As is described above, for example, when employing a multiple exposure method in a photolithography process for manufacturing semiconductor devices, liquid crystal display devices, imaging devices such as CCD, thin film magnetic heads and the like, the use of the present invention makes it possible to perform optimal reticle control, by analyzing the position, size, shape, type, number, density and neighboring exposure pattern of a foreign particle/defect and the like of a plurality of reticles with respect to each combination of the plurality of reticles that are used at the same time, and changing abnormality judgment and/or the subsequent processing based on the analytical results. Therefore, device production with high precision and high throughput becomes possible, which leads to improvement in the yield.

Incidentally, the above disclosures of the various publications, the pamphlets of the International Publications, and the U.S. patent descriptions related to exposure apparatuses and the like that are cited in the embodiment described above are each incorporated herein by reference.

While the above-described embodiment of the present invention is the presently preferred embodiment thereof, those skilled in the art of lithography systems will readily recognize that numerous additions, modifications, and substitutions may be made to the above-described embodiment without departing from the spirit and scope thereof. It is intended that all such modifications, additions, and substitutions fall within the scope of the present invention, which is best defined by the claims appended below.

What is claimed is:

1. A defect detection method with respect to at least one of a plurality of masks that are used for exposure of an area to be exposed on a substrate, the defect detection method comprising:
  obtaining information on an area of a first pattern that is formed on a first mask of the plurality of masks; and
  setting a detection condition that is used in performing the defect detection of a second mask of the plurality of masks based on the obtained information on the area of the first pattern formed on the first mask, the second mask having a second pattern, which is different from the first pattern, in a corresponding area of the second mask that corresponds to the area of the first pattern.

2. The defect detection method according to claim 1, wherein
  when performing the defect detection of the second mask, a foreign particle adhering to a light-transmitting section of the second pattern formed on the second mask is detected.

3. The defect detection method according to claim 2, wherein
  the defect detection of the second mask is performed based on whether a light-transmitting section of the first pattern is formed at a position on the first mask corresponding to a specific position of a light-transmitting section in the second pattern.

4. The defect detection method according to claim 2, wherein
  a detection sensitivity in detecting a foreign particle is adjusted in accordance with the information on the first pattern.

5. The defect detection method according to claim 2, wherein
  a detection result of an output content based on information on the first pattern and a size of a detected foreign particle is output.

6. The defect detection method according to claim 2, wherein
  a frequency of executing the defect detection is based on the obtained information on the first pattern.

7. The defect detection method according to claim 1, wherein
  a foreign particle adhering to the light-shielding section of the second pattern is detected when performing the defect detection of the second mask.

8. The defect detection method according to claim 7, wherein
  in the defect detection a detection result of the foreign particle adhering to the light-shielding section of the second pattern, is output, and
  an output content is based on a size of the detected foreign particle.

9. The defect detection method according to claim 1, wherein
  a detection condition that is used in performing the defect detection of the second mask is set based on whether at least one of an optical proximity correction pattern, a phase shift pattern, a contact hole pattern and a line-and-space pattern in the first pattern is proximate to a position on the first mask that corresponds to a specific position in the second pattern.

10. The defect detection method according to claim 1, wherein
  a detection condition that is used in performing the detection of the second mask is set based on differences in surface shape between a specific position on the first mask corresponding to the specific position in the second pattern.

11. A defect detection apparatus that performs defect detection of at least one of the plurality of masks using the defect detection method according to claim 1.

12. An exposure method in which an area to be exposed on a substrate is exposed a plurality of times with a plurality of patterns, the method comprising:
  performing based on information on an area of a first pattern formed on a first mask, a defect detection of a corresponding area of a second mask that is different from the first mask; and
  controlling an exposure process of the substrate based on a result of the defect detection, wherein
  the corresponding area of the second mask is different than the area of the first pattern.

13. An exposure apparatus that performs exposure using the exposure method according to claim 12.

14. A device manufacturing method comprising:
  exposing a same area on a substrate a plurality of times with a plurality of masks, including a first mask having a first pattern and a second mask having a second pattern, the first pattern being different from the second pattern in corresponding areas;
  obtaining information on the first pattern; and
  based on the obtained information on the first pattern, performing a defect detection of the second mask.

15. The device manufacturing method according to claim 14, the method further comprising:
  cleaning at least one of the first mask and the second mask based on a result of the defect detection of the second mask.

16. The device manufacturing method according to claim 14, the method further comprising:
  exchanging at least one of the first mask and the second mask based on a result of the defect detection of the second mask.

17. The device manufacturing method according to claim 14, wherein
  at least one of the first pattern on the first mask and the second pattern on the second mask is changed based on a result of the defect detection of the second mask.

18. The device manufacturing method according to claim 17, wherein
  at least one of the first mask and the second mask is an electron mask that can change a pattern formed thereon.

19. A device manufacturing system that executes the device manufacturing method according to claim 14.

* * * * *